(12) United States Patent
Matson

(10) Patent No.: US 6,194,217 B1
(45) Date of Patent: *Feb. 27, 2001

(54) METHOD OF DIAGNOSING OR CATEGORIZING DISORDERS FROM BIOCHEMICAL PROFILES

(75) Inventor: Wayne R. Matson, Ayer, MA (US)

(73) Assignee: ESA, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/105,482

(22) Filed: Aug. 12, 1993

Related U.S. Application Data

(63) Continuation of application No. 07/649,676, filed on Feb. 1, 1991, now abandoned, which is a continuation-in-part of application No. 07/643,541, filed on Jan. 18, 1991, now abandoned, which is a continuation-in-part of application No. 07/274,505, filed on Nov. 21, 1988, now Pat. No. 5,104,639, which is a division of application No. 06/797,615, filed on Nov. 13, 1985, now Pat. No. 4,863,873, which is a continuation-in-part of application No. 06/670,483, filed on Nov. 13, 1984, now abandoned, which is a continuation-in-part of application No. 06/579,401, filed on Feb. 17, 1984, now Pat. No. 4,511,659, which is a continuation-in-part of application No. 06/472,387, filed on Mar. 4, 1983, now abandoned, which is a continuation-in-part of application No. 06/425,183, filed on Sep. 28, 1982, now abandoned, which is a continuation-in-part of application No. 06/111,917, filed on Jan. 14, 1980, now Pat. No. 4,404,065.

(51) Int. Cl.$^7$ .................................................. G01N 33/48

(52) U.S. Cl. ............................ 436/63; 436/64; 436/150; 436/161; 73/61.52

(58) Field of Search .............................. 436/63, 64, 150, 436/161; 424/2, 530, 531, 532, 520, 545; 73/61.52, 61.59, 61.61; 204/153.1, 403, 406

(56) References Cited

U.S. PATENT DOCUMENTS

| | | | | |
|---|---|---|---|---|
| 4,338,811 | * | 7/1982 | Mivagi et al. | 73/23.1 |
| 4,343,767 | * | 8/1982 | Long et al. | 422/70 |
| 4,511,659 | * | 4/1985 | Matson | 436/150 |
| 4,654,313 | * | 3/1987 | Hartman | 436/811 X |
| 4,863,873 | * | 9/1989 | Matson | 436/68 X |
| 5,104,639 | * | 4/1992 | Matson | 436/150 X |

OTHER PUBLICATIONS

Matson et al. *Life Sciences,* vol. 41, No. 7, 1987, pp. 905–908.*
Seltzer et al. *Arch Neurol.,* vol. 43, Jul. 1986, pp. 665–668.*
Banissi–Sabourdy et al. *Bioelectrochemistry and Bioenergetics,* vol. 28, 1992, pp. 127–147.*
Dorland et al, "Dorland's Illustrated Medical Dictionary", 1988, p. 461, W.B. Saunders Company.

* cited by examiner

*Primary Examiner*—Maureen M. Wallenhorst
(74) *Attorney, Agent, or Firm*—Hayes, Soloway, Hennessey Grossman & Hage, P.C.

(57) ABSTRACT

A method for diagnosing disorders in a subject organism, in which fluid samples from normal and abnormal organisms are analyzed to generate electrical signal patterns representative of molecular constituents of the samples. A data base of electrical signal patterns representative of frequency distribution of sample constituents from the abnormal organisms having known categories of disorders and control samples from normal organisms are created, and a fluid sample taken from the subject organism is analyzed by comparing it to the data base for conformity to the electrical signal patterns representative of the frequency distribution. The invention has particular applicability to assisting in the diagnosis of degenerative diseases such as Alzheimer's Disease, Parkinson's Disease, Huntington's Disease, schizophrenia, amyotrophic lateral sclerosis and Progressive Supernuclear Palsy.

32 Claims, 8 Drawing Sheets

METHOD OF DIAGNOSING OR CATEGORIZING DISORDERS FROM BIOCHEMICAL PROFILES

This application is a continuation of application Ser. No. 07/649,676 filed on Feb. 1, 1991, now abandoned, which is in part a continuation of my application Ser. No. 07/643,541 filed Jan. 18, 1991, now abandoned, which in turn is in part a continuation of my application Ser. No. 07/274,505, filed Nov. 21, 1988, now U.S. Pat. No. 5,104,639, which in turn is a divisional application of my Ser. No. 06/797,615, filed Nov. 13, 1985 (Now U.S. Pat. No. 4,863,873), which is in part a continuation of my application Ser. No. 06/670,483, filed Nov. 13, 1984 (now abandoned), which in turn is in part a continuation of my application Ser. No. 06/579,401, filed Feb. 17, 1984 (now U.S. Pat. No. 4,511,659), which is in part a continuation of my application Ser. No. 06/472,387 filed Mar. 4, 1983 (now abandoned), and in part a continuation of my application Ser. No. 06/425,183 filed Sep. 28, 1982 (now abandoned), which is in part a continuation of my application Ser. No. 06/111,917 filed Jan. 14, 1980 (now U.S. Pat. No. 4,404,065).

This invention relates to analytical and mathematical methods for diagnosing or categorizing disorders. The invention has particular utility for diagnosing or categorizing disorders in living animals from analysis profiles of biologically active materials such as neurotransmitters and other neurochemical substances in brain tissue, cerebrospinal fluid, plasma, serum, saliva, nasal mucosa, urine and the like, such as catecholamines, their precursors, cofactors and their metabolites. The invention is uniquely capable of differentiating a large number of compounds of biological, diagnostic and/or pharmaceutical significance and of using such differential for diagnosing disorders and will be described in connection with such utility although other uses are contemplated.

There is an extensive body of literature relating abnormalities in neurotransmitters, precursors, and metabolites to degenerative, neuropsychiatric and behavioral disorders, hypertension and certain carcinomas. See, for example, Schildkraut et al in *The Brain, Biochemistry and Behavior*, Proceedings of the Sixth, Arnold O. Beckman Conference in Clinical Chemistry, pages 47–68. Although the potential role of these compounds in a number of significant disorders has been established, their routine analysis has not yet achieved widespread clinical use. Two problems in the clinical utility of neurotransmitter measurements are related to the economic and technical limitations of current technology. First, there is felt to be a high degree of interlaboratory and intersample uncertainty in quantitative values. Second, it has been difficult to measure enough of the known metabolically related compounds of a particular neurotransmitter to fully describe its biochemical significance in an individual sample, or to detect, identify and measure unusual neurotransmitters—an important aspect of basic research in various disease states that is presently very expensive and specialized.

While a number of interlaboratory technique intercomparisons for a variety of neurotransmitters have been carried out, there has been no comprehensive study within and among different techniques and laboratories for neurotransmitters in typical samples of interest. In the absence of such studies, given the complexity of the analytical problem and the historically wide variation whenever an analyte has been subjected to rigorous interlaboratory testing, the current values for normal and abnormal neurotransmitter levels must be taken with unspecified and probably wide limits of confidence.

Although the analysis of single neurotransmitters or metabolites from a complex biochemical pathway has been shown to correlate with a number of disorders utilizing statistical analysis over a larger number of samples, the analytical level of a single neurotransmitter in an individual sample, with a few exceptions, has had relatively low clinical diagnostic utility. Essentially the state of the field of biochemical correlates of disorders is that while between large populations of normal and abnormal individuals a correlation generally can be determined for a particular biochemical, the scatter that results from both analytical and biochemical phenomena typically does not permit the level of a particular biochemical to be utilized diagnostically for a particular single individual. Nor may a single biochemical value be utilized for the rational prescription or development of a pharmaceutical for that individual. This is not particularly surprising in that both the levels and effects of a particular neurotransmitter are modified by a number of other neurotransmitters, in the same, or parallel metabolic pathways. If, for instance, 5-HT (serotonin) is to be used as a diagnostic tool for depression, suicidal tendencies, or schizophrenia, it would be necessary and perhaps provide a route to definitive diagnosis and pharmaceutical specification or development, to simultaneously determine the approximately 40 other compounds that derive from tryptophan and significantly effect the indolaminergic neuronal system's activity.

In recent years, LCEC (Liquid Chromatography with Electrochemical Detection) has become a common tool for the determination of catacholamines biogenic amines and their metabolites in biological fluids. Because of sensitivity limitations (typically 20–50 pg) and the complexity of biological samples, both separation and concentration steps typically have been necessary. Heretofore, plasma catecholamine analysis typically required three steps. First, the sample is collected and the catecholamines separated and concentrated, for example, using the alumina extraction procedure of Anton and Sayre (See A. H. Anton and D. F. Sayre, J. Pharmacol, Exp. Ther., 138 (1962), p. 360–375). The analytes, norepinephrine, epinephrine and donamine, along with the internal standard DHBH (dihydroxybenzylamine), then are separated chromatographically, and finally detected electrochemically. Typical sample size requirements are 1.0 ml plasma or serum. In routine clinical use, there have been numerous problems with conventional techniques (alumina absorption, ion exchange and extraction), due to a large number of poorly understood variables, in the overall analysis system of sample acquisition, storage, preparation and sensor response. These problems have quite likely confused the relationships that may exist between levels and distribution of the catecholamines and various physiological and behavioral phenomena and disease states.

In the analysis of complex biological materials such as blood, serum and cerebrospinal fluids which may contain numerous different constituents, the important (e.g. abnormal) metabolites such as neurotransmitters to be identified may be present in only parts per trillion. While a chromatographic column can achieve macro separation of the various constituents, it may not provide adequate spatial (in time) separation of the extremely small portion of metabolites of interest from the much larger percentage of the many other compounds coeluted from the column at the same time as the metabolites of interest. Many of these interfering coeluted materials are electrochemically active but electrochemically irreversible, while many metabolites such as neurotransmitters are both electrochemically active and electrochemically reversible. It has been found that the analytical problems of reliable measurements of neurochemicals and related compounds are complicated by the fact that interferences with conventional or prior technologies are disorder related. This was discussed in my prior publication, (Matson et al. Clinical Chemistry, Vol. 30, No. 9, 1984) (see U.S. Pat. No. 4,511,659) for dopamine, dopac and seratonin measurements in directly analyzed brain extract and cerebrospinal fluid for normal, schizophrenics and Alzheimers. Recent work has indicated that even for the widely used and accepted technique of alumina extraction for plasma catecholamines that interferences may be disorder specific. Higher values for Norepinephrine (NE) and Epinephrine (EP) were observed following alumina extraction and analysis of a single energy conventional electrochemical detector than for a three cell redox detector on neonatal stress blood samples. Analysis of the neonate extracts on the sixteen channel chemical imaging system revealed several unexpected compounds that are potential interferences including dihydroxyphenylacetic acid (DOPAC), 3 hydroxykynurenamine (3-OHKYA) and 3-hydroxy-anthranilic acid (3-OHAN). These compounds have not been detected in normal adult plasma alumina extracts.

In my aforesaid U.S. Pat. No. 4,511,659, there is provided an electrochemical detection system comprising a plurality of coulometrically efficient electrochemical cells, in series, for sequentially oxidizing and reducing selected substances in a sample solution under controlled conditions prior to measurement on a downstream testing electrode or electrodes. More specifically, in accordance with the invention provided in my aforesaid U.S. Pat. No. 4,51,659, a sample solution (e.g. a body fluid) is passed through a suitable chromatographic column and the eluant is streamed in contact with a series of electrochemically isolated, in-line coulometric electrodes operated under conditions so as to establish a series of "gates" for the sequential oxidation and reduction of substances in the sample solution whereby to screen (remove) selected interfering and electrochemically irreversible substances contained in the sample solution, while passing selected electrochemically reversible products for detection and measurement on a downstream electrode. The gate electrode series is follows in-line by one or more, preferably an array of six or more coulometric measuring electrodes, each formed of porous electrode base material such as fritted graphite, fritted carbon or other conductive fritted material, for detecting and measuring the electrochemically reversible compounds of interest (e.g. neurotransmitters).

As reported in my aforesaid U.S. Pat. No. 4,511,659, there are several beneficial effects of this approach to electrochemical analysis. Long-term drift in response is effectively eliminated by acquiring essentially 100% of the signal. The capability of analyzing essentially 100% of a material allows the assay of compounds of unknown purity by relating them to the basic principles of electrochemical reaction embodied in Faraday's Law. Poisoning of the electrode, a dominant problem with electrochemical sensors, is effectively eliminated by the use of a much larger relative surface area for reaction. And, finally, and most important to the eventual development of array and gate cells, a coulometric electrode by virtue of its essentially 100% efficiency allows sequential oxidation and/or reduction of compounds at successive-in-line detectors. The improved sensitivity of the detection system as discussed in my aforesaid U.S. Pat. No. 4,511,659, particularly where two or more active testing electrodes follow the screening electrodes has given the ability to do direct injections of serum filtrates and has also allowed the generation of reproducible patterns of compounds with catecholamine like electrochemical behavior of a large number of resolvable components. This provides the possibility of performing pattern recognition for the diagnosis or perhaps even predictive diagnosis, of various disorders or disease states.

In my copending application Ser. No. 797,615 and its parent U.S. Pat. No. 4,863,873, I describe a system for resolving and detecting hundreds of compounds in a single sample at femtogram levels whereby to provide a small molecule inventory or metabolic pathway pattern of an individual. As taught in my aforesaid U.S. Pat. No. 4,893,873, the small molecule inventory may be considered to reflect the underlying activity and distribution of the enzymatic pathways of an individual and hence reflect an operational measure of the genome determining those enzymes. The small molecule inventory of an individual may thus be used to determine the health state of the individual and/or to diagnose disease states. Correlation of the patterns from a plurality of individuals provides an understanding of the mechanisms of disorders or disease states or conditions and, in turn, provides a rational route to pharmacological development leading to treatment, cure or suppression of such disorders, disease states of conditions.

The present invention is an improvement in the invention described in my aforesaid U.S. Pat. No. 4,863,873. More particularly, in the practice of my invention as described in my U.S. Pat. No. 4,863,873, I have observed that the biochemical analysis profiles of "normal" or healthy individuals may vary quite widely, while the biochemical profile analysis data of individuals having disorders is far less chaotic. More particularly, I have observed that the frequency distribution of certain biochemical compounds or ratios of compounds in individuals suffering from a disorder are far less chaotic than "normal" or healthy individuals. This leads to a general protocol for diagnosing, categorizing or differentiating individuals based on comparisons of biochemical analytical data of small molecule inventory against data bases (which may be of epidemiologically significant size) of known or previously diagnosed cases. By way of example the process of the present invention may advantageously be employed in the differentiation of neurological degenerative dementing or affective disorders such as Alzheimer's disease, Huntington's disease, Parkinson's disease, schizophrenia, Progressive Supernuclear Palsy, amyotrophic lateral sclerosis and senile dementias from each other and neurologically normal controls. Moreover, by suitable selection of variables, the process of the present invention also is applicable to classification of tumors, carcinomas, cardiovascular abnormalities and other disorders. Similarly, the process of the present invention advantageously may be utilized to select therapy based on categories of known successful vs. unsuccessful outcomes.

While not wishing to be bound by theory, the two fundamental hypotheses underlying the process of the present invention are:

1. The underlying genetic makeup or predisposition of an individual will reflect through the proteins, enzymes, and other factors it determines in patterns of small molecules. Individual components within these patterns will be affected by environmental effects such as diet, stress or chemical inset; however, the overall pattern of relationships will reflect the underlying operation of the genome or the interference of a particular disorder. Among the small molecules are the transmitters, cofactors and metabolites that regulate neuronal and endocrine functions and the interactions of somatic and central nervous system processes. Thus, the compounds such as purines, tyrosine and tryptophan derived neurotransmitters, peptides, pterin and vitamin cofactors are highly relevant to the effect or etiology of neurological disorders, cardiovascular disfunction and certain tumors or carcinomas.

2. The relationships of these biochemical patterns from a disorder are less chaotic or more regular than those from healthy controls. All of the biochemical systems of small molecules are interconnected and interrelated in a complex web of feedback and response. These interactions are highly nonlinear and thus, depending on subtle differences in initial conditions, the response of individual components in a biochemical pattern will be highly variable. The overall system will thus behave in a mathematically chaotic fashion. In a disorder, elements within the biochemical pattern are over or underregulated, thus reducing the degrees of freedom or overall variability. Consequently, the presence of a disorder implies more regulated or less chaotic variability of compounds or relationships among compounds in patterns from disordered individuals.

These two fundamental hypotheses provide an approach to diagnostic categorization of disorders using frequency distributions of compounds and relationships from large data bases.

DESCRIPTION OF THE DRAWINGS

For a fuller understanding of the nature and objects of the present invention, reference should be had to the following detailed description taken in combination with the accompanying drawings wherein.

DETAILED DESCRIPTION OF THE INVENTION

EXAMPLE I

Figure 1A:
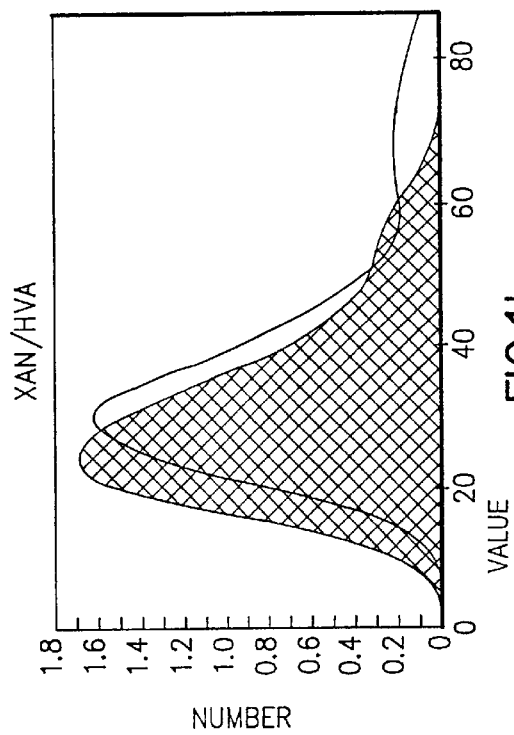
FIGS. 1a–1d are frequency distribution graphs of variables of Alzheimer's Disease and controls.
Figure 1B:
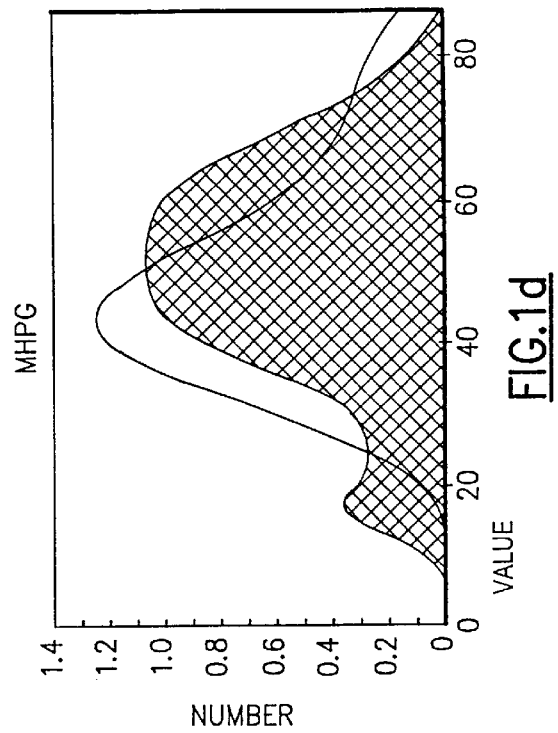
Figure 1C:
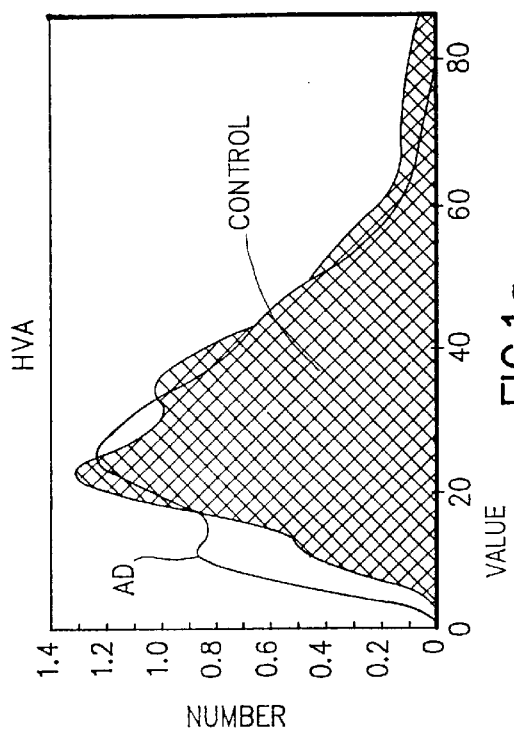
Figure 1D:
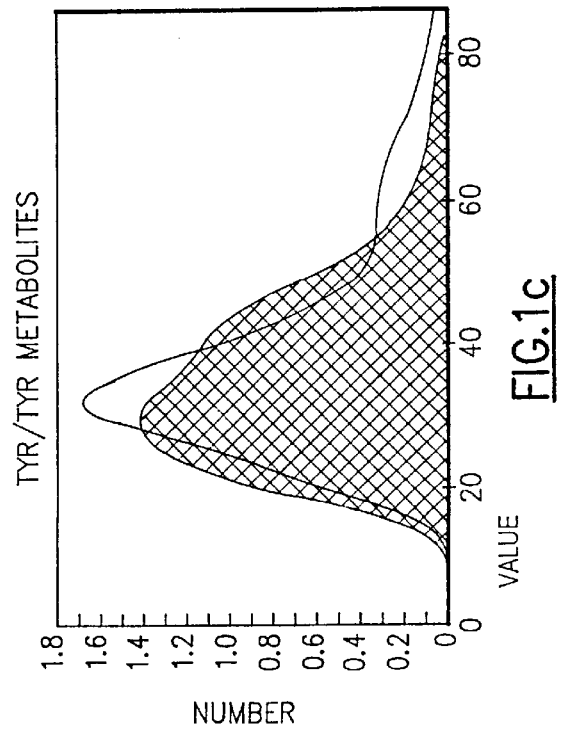

Methodology for Sample Analysis and Data Base Creation 280 cerebrospinal fluid (CSF) samples from the categories Alzheimer's Disease—AD (61 samples), Parkinson's Disease—PD (60 samples), schizophrenia—SC (60 samples), Huntington's Disease—HD (20 samples), Supernuclear Palsy—PSP (13 samples) and neurologically normal controls—C (68 samples), were electrochemically analyzed in accordance with the teachings of my aforesaid U.S. Pat. No. 4,863,873. Samples from normal and diseased individuals were prepared and flowed through a chromatographic column, and detected in a 16 sensor electrochemical cell using an NCA Chemical Analyzer, Model No. CEAS available from ESA, Inc., Bedford, Mass. Sensor potentials ranged from $T_1$ −600 mv to $T_{16}$ +900 mv in 100 mv increments. All samples were from 7th or 8th mL aliquots of nostril caudal gradients. Pools were created for each category utilizing small subaliquots of the samples, and pools of all samples were created for analytical quality control and evaluation of unknowns. Samples were run under a variant of a standard reverse phase gradient procedure in the repetitive sequence Control Standard, Pool, 7 Samples, Control Standard, Pool, . . . as set forth in Table 1.

Table 1 Characteristics of Method 1

Real time set up review; Times and events in the methods chromatographic functions.

Review of live method: Potentials and currents of channels 1–16 range functions temperature and limits.

TABLE 1

REAL TIME SETUP REVIEW

|   | TIME | DEVICE | FUNCTION | VALUE | TOTAL |
|---|------|--------|----------|-------|-------|
| 1 | 0.00 | FLOW | % B | 5 | 1.20 |
| 2 | 0.20 | CLEAN CELL | ON | 960 | |
| 3 | 0.50 | CLEAN CELL | OFF | | |
| 4 | 7.00 | AUTO ZERO | ON | | |
| 5 | 7.58 | FLOW | % B | 5 | 1.20 |
| 6 | 7.58 | AUTO SAMPLER | INJECT | | |
| 7 | 8.00 | FILE | START | | |
| 8 | 66.00 | FLOW | % B | 94 | 1.06 |
| 9 | 66.00 | FLOW | % B | 5 | 1.20 |
| 10 | 70.00 | FILE | STOP | | |
| 11 | 70.00 | FLOW | % B | 5 | 1.20 |
| 12 | 70.00 | AUTO SAMPLER | STEP | | |
| 13 | 70.00 | END | | 2 | |
| 14 | 70.00 | METHOD | M147 | | |

REVIEW OF LIVE METHOD

| Full Scale Current | | | | P'stats | | | | Autorange On |
|---|---|---|---|---|---|---|---|---|
| 10 uA | 100 uA | 10 uA | 10 uA | −40 mV | 25 mV | 90 mV | 155 mV | |
| 1 uA | 1 ua | 10 uA | 1 uA | 220 mV | 285 mV | 350 mV | 415 mV | Floor |
| 1 uA | 1 uA | 1 uA | 1 uA | 480 mV | 545 mV | 610 mV | 675 mV | 100 nA |
| 1 uA | 1 uA | 1 uA | 1 uA | 740 mV | 805 mV | 870 mV | 910 mV | |

Cell Box Temp: 35.° C.

| | UPPER LIMIT | LOWER LIMIT |
|---|---|---|
| PUMP A: | 350 | 0 |
| PUMP B: | 350 | 0 |

| VALVE: | POS1 |
|---|---|
| Mobile Phase: | |

| A. | 0.05 M LiH$_2$PO$_4$, pH 2.86, 3 mg/L Lithium Dedecyl Sulfonic Acid |
|---|---|
| B. | 30% MeOH, 0.05 M LiH$_2$PO$_4$, pH 2.86, 3 mg/L Lithium Dodecyl Sulfonic Acid |
| Column: | Dual 5u ODS, 4.6 mm × 15 cm ESA NBS |

Samples were analyzed for 38 known components (listed in Table 2) and for 18 well-defined unknown peaks that were isolated in all pools shown in Table 3. (Asterisks denote components used in evaluation of regression and cluster analysis statistical procedures for categorization of groups.)

Table 2

Oracle compatible record showing retention times, digitized characteristic responses across channels, and set of control standard. Abbreviations are described in Table 6.

TABLE 2

Sat. Nov. 18 17:15:22 1990
Standard std0001
Table: NOY8STD
Study: CSFRUX01
Identified Compounds in Standard: 38
Missing Compounds in Standard: 8

| # | File RT | Name Conc | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 1 | std0001 1.725 | ASC 10000.00 | 1.717 3872279 | 1.700 9625125 | 1.725 1.27e+07 | 1.725 1.60e+07 | 1.750 1.50e+07 | 1.733 1.14e+07 | | | | | | | | | | |
| 2 | std0001 2.283 | CYS 1000.00 | | | | | | | | | | | | | | | | |
| 3 | std0001 2.350 | URIC 8000.00 | | | 2.333 5672 | 2.342 1324197 | 2.350 3193191 | 2.350 1019128 | 2.267 129467 | 2.267 251043 | 2.258 528682 | 2.267 1298734 | 2.275 1601456 | 2.283 2250767 | 2.292 1062584 | | | |
| 4 | std0001 3.058 | XAM 8000.00 | | | | | | | | | 3.042 47171 | 3.033 1393667 | 3.058 3304889 | 3.067 2039171 | 3.067 350667 | 3.108 110509 | | |
| 5 | std0001 3.125 | HX 100.00 | | | | | | | | | | | | | | 3.108 110609 | 3.117 154070 | 3.125 16113 |
| 6 | std0001 4.875 | VMA 10.00 | | | | 4.883 387 | 4.867 4959 | 4.875 16674 | 4.875 13957 | | | | | | | | | |
| 7 | std0001 4.900 | GSM 500.00 | | | | | | | 4.875 13957 | 4.875 28075 | 4.875 51532 | 4.875 117237 | 4.892 133772 | 4.900 197987 | 4.908 85618 | | | |
| 8 | std0001 5.642 | NE 10.00 | 5.625 334 | 5.642 18928 | 5.642 17463 | 5.650 1507 | 5.650 117 | | | | | | | | | | | |
| 9 | std0001 6.075 | MHPG 10.00 | | | | | 6.075 749 | 6.075 13983 | 6.075 5545 | 6.075 1828 | 6.083 1718 | 6.092 1044 | | | | | | |
| 10 | std0001 6.382 | HGA 10.00 | 6.392 16607 | 6.408 4974 | | | | | | | | | | | | | | |
| 11 | std0001 7.942 | C 100.00 | | | | | | | | | 7.942 2395 | 7.942 122100 | 7.950 53287 | 7.958 4420 | 7.958 975 | | | |
| 12 | std0001 9.150 | GR 500.00 | | | | | | | | | | 9.142 859 | 9.123 26558 | 9.125 194121 | 9.142 430593 | 9.150 1054244 | 9.175 189936 | 9.192 11191 |
| 13 | std0001 9.263 | LD 10.00 | 9.326 165 | 9.283 10336 | 9.283 14153 | 9.292 1156 | 9.275 562 | | | | | | | | | | | |
| 14 | std0001 9.650 | HET 500.00 | | | | | | | | | | 9.462 986 | 9.642 6461 | 9.650 26013 | 9.650 33548 | 9.650 107932 | 9.667 86595 | 9.675 31459 |
| 15 | std0001 10.008 | AM 100.00 | | 10.142 14152 | 10.150 9783 | 10.008 33745 | 10.008 118573 | 10.017 17512 | 10.000 2328 | | | | | | | | | |
| 16 | std0001 10.142 | EPI 10.00 | 10.167 367 | | | | | | | | | | | | | | | |
| 17 | std0001 10.217 | EPI A 100.00 | | | | | | | | | | | | | | | 10.250 26046 | 10.217 36349 |
| 18 | std0001 11.833 | DOPAC 10.00 | 11.825 247 | 11.833 7794 | 11.833 9749 | 11.842 1412 | 11.850 443 | 11.833 251 | | | | | | | | | | |
| 19 | std0001 13.200 | 30HAN 10.00 | | 13.225 1194 | 13.200 29905 | 13.217 8215 | 13.242 2107 | 13.250 1401 | | | | | | | | | | |
| 20 | std001 13.200 | 30HXY 10.00 | | 13.225 1194 | 13.200 29905 | 13.217 8215 | 13.242 2107 | 13.250 1401 | | | 13.442 | 13.450 | 13.467 | 13.458 | | | | |
| 21 | std0001 13.217 | 4HPLA | | | | | | | | | 13.442 | 13.450 | 13.467 | 13.458 | | | | |

TABLE 2-continued

Sat. Nov. 18 17:15:22 1990
Standard std0001
Table: NOY8STD
Study: CSFRUX01
Identified Compounds in Standard: 38
Missing Compounds in Standard: 8

| # | File RT | Name Conc | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 22 | 13.450 std0001 13.692 | XMN 10.00 | | | | | 13.683 1593 | 13.692 14780 | 13.683 3917 | | 13364 | 125434 | 43118 | 2233 | | | | |
| 23 | 13.992 std0001 13.992 | 4HBAC 200.00 | | | | | | | | | | | 13.983 75738 | 13.992 207495 | 13.992 311864 | 14.008 170423 | | |
| 24 | std0001 15.233 | TYR 1000.00 | | | | | | | 15.250 232 | 15.242 3866 | 15.225 102584 | 15.233 1181673 | 15.250 776764 | 15.250 117510 | 15.292 | | | |
| 25 | std0001 15.592 | 5HTP 10.00 | | | 15.583 6994 | 15.592 16297 | 15.617 463 | | | | | | | | | | | |
| 26 | std0001 17.342 | DA 10.00 | | 17.342 17722 | 17.342 6301 | 17.358 305 | 17.367 144 | | | | | | | | | | | |
| 27 | std0001 17.892 | 5HIAA 50.00 | | 17.850 233 | 17.892 9330 | 17.892 119759 | 17.908 14604 | 17.375 8313964 17.925 549 | | | | | | | | | | |
| 28 | std0001 18.100 | 4PAC 200.00 | | | | | | | 18.063 80 | 16.117 1343 | 18.092 37258 | 18.200 461257 | 18.125 267050 | | 18.075 59412 | 18.117 112086 | 18.167 54548 | 18.175 38306 |
| 29 | std0001 18.117 | XYA 50.00 | | | | | | | | | | | | | | | | |
| 30 | std0001 31.602 | 3OHD 10.00 | | | | | | | | | | | | | | | | |
| 31 | std0001 22.200 | 5HTDL 10.00 | | 22.167 47 | 22.200 1668 | 22.575 58 22.200 19401 | 21.608 2183 22.217 1931 | 21.608 11525 | 21.600 2176 | 21.592 143 | | | | | | | | |
| 32 | std0001 23.917 | HVA 200.00 | | | | 23.925 125 | 23.925 13994 | 23.917 237705 | 23.917 163964 | 23.925 47292 | 23.925 8852 | 23.950 2293 | | | | | | |
| 33 | std0001 24.258 | XTX 100.00 | | | | | | | | | | | 24.287 101620 | 24.258 108998 | 24.283 55261 | 24.300 38928 | 24.308 21718 | 24.308 4609 |
| 34 | std0001 24.492 | TYRA 80.00 | | | | | | | | | 24.475 2368 | 21.492 28935 | 21.517 5390 | | | | | |
| 35 | std0001 30.792 | 5HT 10.00 | | 30.742 231 | 30.783 6953 | 30.792 9627 | | | | | | | | | | | | |
| 36 | std0001 31.975 | 3HT 10.00 | | | | 31.967 143 | 31.975 11501 | 31.975 33026 | 31.967 2425 | 31.975 171 | | | | | | | | |
| 37 | std0001 41.467 | TPOL 100.00 | | | | | | | 41.500 375 | 41.475 2006 | 41.458 7109 | 41.467 9905 | 41.492 4810 | | | | | |
| 38 | std0001 45.292 | TRP 700.00 | | | | | 45.350 615 | 45.342 8371 | 45.388 23358 | 45.300 248497 | 45.275 967515 | 45.292 2056846 | 45.325 1090677 | 45.350 187013 | 45.350 109610 | | | |

TABLE 3

Tue Dec 18 11:43:57 1990
Sample Report            Page 1
Sample: POOL37
Standard:
Table: POOL19A
Study: CSF19A
Compounds identified: 22
Known Compounds Not Found: 0
Unknown Peak Clusters: 745
Compounds Identified

| Compound | Conc | RT | RT Error | Height | Ratio Accurac |
|---|---|---|---|---|---|
| *p01 | 104.413971 | 2.617 | 0.100 | 167971 | 7/6 0.999 |
| XAN | 973.750732 | 2.900 | 0.117 | 756026 | 10/11 12/11 0.861 0.959 |
| *p02 | 101.869156 | 3.108 | 0.125 | 208822 | 15/16 0.666 |
| p03 | 131.687439 | 5.733 | 0.275 | 2747 | |
| p04 | 106.228569 | 8.242 | 0.325 | 142085 | 13/14 15/14 0.977 0.891 |
| TYR | 979.260254 | 13.567 | 0.692 | 1375195 | 9/10 11/10 0.987 0.977 |
| *P05 | 99.553802 | 14.633 | 0.583 | 52515 | 13/14 0.949 |
| P09 | 89.990860 | 15.117 | 0.650 | 7632 | 9/10 11/10 0.850 0.923 |
| P07 | 92.967072 | 15.275 | 0.600 | 55664 | 14/15 0.951 |
| P08 | 96.659180 | 16.133 | 0.417 | 29579 | 10/11 0.976 |
| *P10 | 96.603462 | 21.875 | 0.942 | 42516 | 9/10 0.949 |
| HVA | 195.139450 | 22.475 | 0.800 | 30508 | 5/6 7/6 0.987 0.921 |
| P11 | 102.689194 | 24.892 | 0.717 | 16233 | 16/15 0.892 |
| P12 | 91.103188 | 25.150 | 0.850 | 10652 | 9/10 0.951 |
| *p18 | 98.121086 | 26.850 | 1.308 | 470 | |
| *p19 | 121.804512 | 27.192 | 1.142 | 324 | |
| P13 | 96.415916 | 28.158 | 0.883 | 53718 | 12/13 0.960 |
| P14 | 97.315338 | 29.542 | 1.108 | 24489 | 13/14 0.969 |
| P15 | 94.104630 | 29.642 | 1.100 | 10631 | 9/10 0.916 |
| P16 | 88.826569 | 32.425 | 0.767 | 2937 | 10/11 0.761 |
| P17 | 96.782722 | 37.992 | 1.133 | 22787 | 13/14 0.958 |
| TRP | 674.284607 | 42.150 | 1.583 | 277999 | 9/10 11/10 0.979 0.966 |

The analysis records were linked by a unique identifier to clinical data of clinical diagnosis, diagnostic criteria, age, pharmaceutical history, sex and race. Pools analyzed as samples against standards for known values were utilized to assess the precision of known compound values in the data base. Standards sequentially analyzed against identical standards were used as a measure of instrumental performance and pools sequentially analyzed against identical pools were utilized as a measure of the precision of unknown peaks.

Validation of the Data

Control standards analyzed against sequential control standards yielded precision values ranging from ±1%–±4% CV (coefficient of variation) with no outlying values. Pools analyzed as samples gave precision values ranging from ±2–±7% CV for compounds present at the 0.5 ng/mL level or greater and typically ≅25–30% for compounds present at 2x the detection limit of 0.02–0.03 ng/mL (e.g. 5 HT, EPI). Pools sequentially analyzed against identical pools for unknowns gave values of ±3–±15% coefficient of variation. Typically, the coefficient of variation of the pools was 5–25 fold less than the coefficient of variation of analytes in a group of samples. Essentially, the contribution of assay variability to the results is minimal.

The data base, upon completion, contained 280 samples by 57 analytes (17,000 records). Of these, 163 were null either because no peaks were detected at the sensitivity limits of the assay, or because a signal detected did not meet the qualitative criteria for purity.

Regression Analysis

Linear regression analysis and stepwise regression analysis were used in a preliminary evaluation of the data. Both raw and mean corrected data was evaluated.

Regression comparison of the AD group (61) vs. controls (60) setting AD=1 and C=0 gave a categorical separation regression equation with an S (standard error of estimate) value=0.39 and p (the probability that the sample belongs in one group and not in another) value=0.0041 for 27 of the most significant known compound variables identified in stepwise regression (labeled with asterisks in Table 2). Inclusion of 7 of the most significant variables (labeled with asterisks in Table 3) from the pool analyzed unknown peak data base gave values of S=0.382 and p=0.0037. Assuming a clinical diagnostic error rate in the order of 10%, seven AD samples with regression calculated values (from −1.2 to 0.01) were removed from the calculation. The regression characteristics were then S=0.352 and p=0.0031.

Regression of the AD group with AD=1 vs. all others (219)=0 for the same variable group yielded an equation with S=0.481 and p=0.0013.

Observations: Although the AD group is separated from other groups with a high degree of probability, there is too high a degree of overlap for a simple linear regression algorithm to accurately categorize an individual sample.

Cluster Analysis Procedures

Cluster analysis procedures using nearest neighbor and furthest neighbor approaches were applied to the data base. With both these approaches, the AD group tended to cluster, but controls were scattered relatively evenly, both outside and inside the AD region. Thus, the cluster analysis approach is not suitable as a categorization tool for this type of data.

Observations: The behavior of the data under cluster analysis protocols, and the observations that the standard deviations of compound values and of precursor/product ratios across metabolic pathways within a disorder group are smaller than within control groups is consistent with the hypothesis that the biochemical response of controls or normal individuals is more chaotic than that of disordered individuals.

Frequency Distribution Probability Analysis

The observations on the nature of the data distributions coupled with the technical ability to run large numbers of samples and variables offers an approach to categorization based on differences in the frequency distributions of variables in different disorder categories. This approach relies on basic probability considerations without any assumptions on the shape of a distribution curve or linearity of relationships.

The simplest question that I have investigated for the preliminary data base is that given an unknown sample, what is the probability (p) that that sample belongs in one group and not another.

For one variable, the question takes the form:

$$P = \frac{(f(V_1))_A}{(f(V_1))_A + (f(V_1))_B}$$

where $F(V_n)_A$ or $f(V_n)_B$=the frequency with which an unknown sample value $(V_n)$ occurs in category A or category B.

For multiple compounds, the expression expands:

$$P = \frac{(f(V_1))_A \cdot (f(V_2))_A \ldots (f(V_n))_A}{(f(V_1))_A \cdot (f(V))_A \ldots (f(V_n))_A + (f(V_1))_B \cdot (f(V_1))_B \ldots (f(V_n))_B}$$

If all frequencies are the same, the P value is 0.5 or a 50/50 chance that the unknown sample is A and not B. A positive answer compresses the expression to a 1 and a negative answer to 0.

Like cluster procedures and unlike regression, the use of the algorithm is independent of the number of variables used.

Implementation of the Procedure

Figure 2:
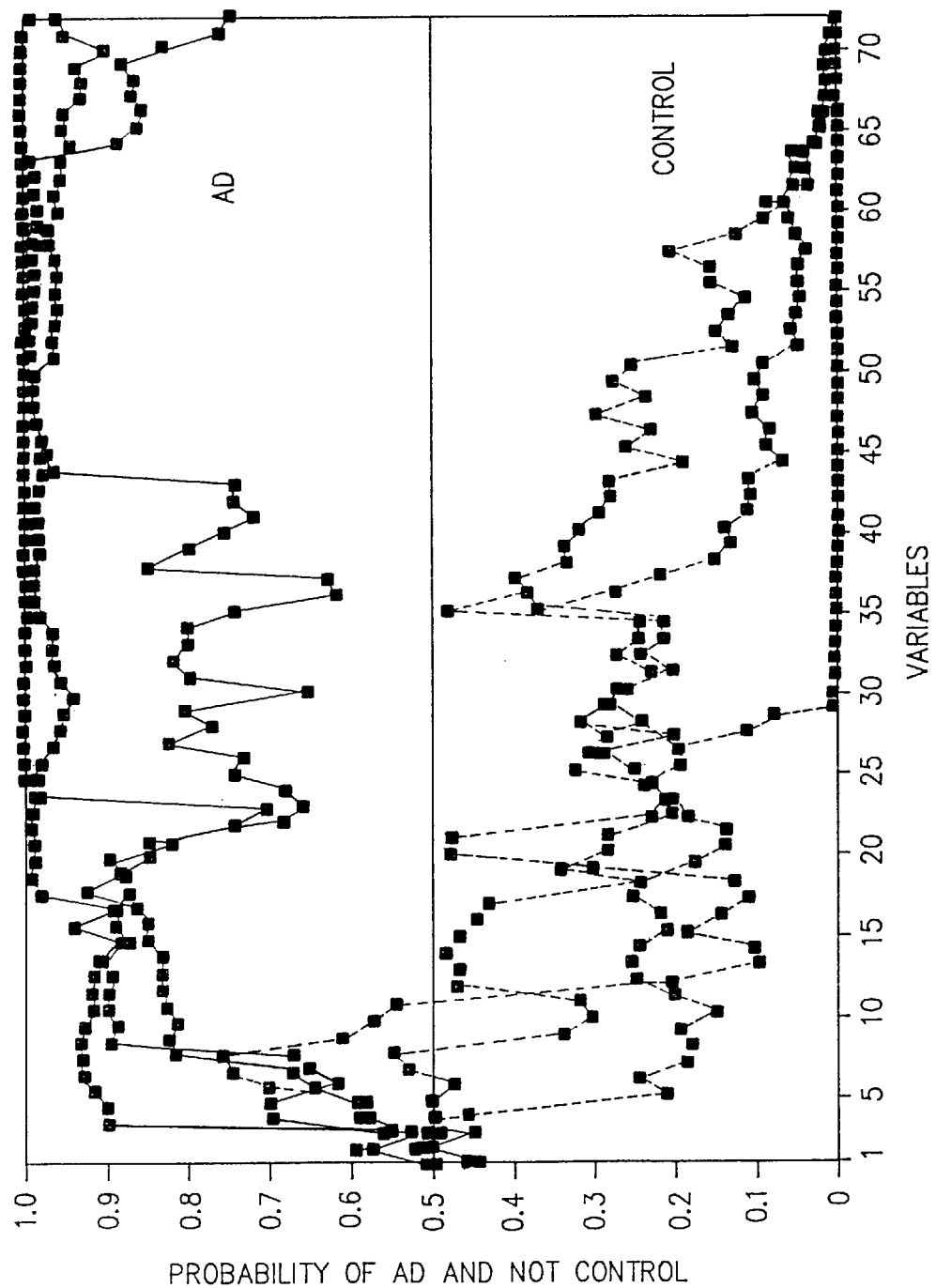
FIG. 2 is a geographical representation of scoring algorithms.

The implementation of the procedure is by the following steps:

1. Frequency distributions (shown in FIGS. 1a–1d) were created by using a smoothing algorithm based on a 3 point polynomial expansion function that treats each point in the sparse data distribution with equal weighting as the means of a distribution with a width at half height proportional to its value. The use of smoothing functions is a necessary assumption until the number of samples in a particular category reaches approximately 300–400. The procedure used was to divide all data in the categories by the maximum value among categories ×85, apply the polynomial expression algorithm, and normalize the data distributions for the number of samples in each category. The frequency distributions in each category are then organized into look up tables for each variable (Table 4) is then inserted into the look up table. Individual values are divided by the range value ×85 and the frequencies for each variable for category A and B are sequentially calculated in the algorithm after subtracting the effect of that sample from the frequency table. The effect of a sequential calculation across a group of variables listed and described in Table 6 is shown in FIG. 2 for 3 AD and 3 C cases from a group of 61 AD and 44 controls. One of the major features of the algorithm is that no single variable predominates as a differentiator among a large group of samples.

Table 4 Distribution Table

The table shows frequency distribution intervals 1–85 for two of the 71 variables in a look up table initially used in scoring AD and control samples.

The tables are obtained by dividing all data by the highest value for the combined data base times 85.

The raw distribution is then smoothed by a polynominal expansion which treats each value with equal weighting as the means of a distribution whose scatter increases with the value.

The overall distributions of groups are normalized to the same area.

TABLE 4

DISTRIBUTION TABLE

| | HVA AD | CONTROL | | MHPG AD | CONTROL |
|---|---|---|---|---|---|
| 1 | 0.010377 | 0.000205 | 1 | 1.2E-10 | 0.000000 |
| 2 | 0.045259 | 0.001702 | 2 | 0.000000 | 0.000003 |
| 3 | 0.126131 | 0.007945 | 3 | 0.000000 | 0.000026 |
| 4 | 0.242295 | 0.025793 | 4 | 0.000000 | 0.000140 |
| 5 | 0.379120 | 0.064431 | 5 | 0.000000 | 0.000576 |
| 6 | 0.503888 | 0.129976 | 6 | 0.000001 | 0.001932 |
| 38 | 0.798418 | 0.938551 | 38 | 1.117459 | 0.742461 |
| 39 | 0.761982 | 0.889793 | 39 | 1.160736 | 0.801194 |
| 40 | 0.730955 | 0.836392 | 40 | 1.196534 | 0.855713 |
| 83 | 0.006846 | 0.088021 | 83 | 0.225452 | 0.069938 |
| 84 | 0.005088 | 0.081885 | 84 | 0.208132 | 0.064130 |
| 85 | 0.003699 | 0.075893 | 85 | 0.190170 | 0.041177 |

DATACASE RECORD

| | C AT0022 | DISTRIBUT RANGE |
|---|---|---|
| MT3 | 0.018080 | 1 |
| OHAN3 | 0.018080 | 3 |
| OHKY3 | 0.090402 | 4 |
| 3OMD | 1.970763 | 44 |
| HVA | 58.03809 | 56 |
| MHPG | 8.714754 | 62 |
| 12 | 2911604 | 22 |
| P01 | 5725159 | 9 |
| P02 | 1359827 | 49 |
| P03 | 1808040 | 1 |

Table 6. Description of Scoring Variables

The table shows the arbitrary sequency in which 71 variables were applied to the initial scoring of AD vs. C (See FIG. 2).

The order of scoring has no effect on the final outcome. Acetaminophen which was included in the assays was not used as a scoring variable.

The table also contains the names of the known compounds assayed and the probable moieties in the unknown peaks inferred from the chromatographic/electrochemical data and in vitro studies. Pathway ratios one to twelve are calculated as molar ratios.

TABLE 6

DESCRIPTION OF SCORING VARIABLES

| Variable Number | Abbreviation | Name or Possible Characteristic |
|---|---|---|
| 1 | 3MT | 3-Methoxytyramine |
| 2 | 3OHAN | 3-Hydroxyanthranilic Acid |
| 3 | 3OHKY | 3-Hydroxykynurenine |
| 4 | 3OMD | 3-0-Methyldopa |
| 5 | 4HBAC | 4-Hydroxybenzoic Acid |
| 6 | 4HPAC | 4-Hydroxyphenylacetic Acid |
| 7 | 4HPLA | 4-Hydroxyphenyllactic Acid |
| 8 | 5HIAA | 5-Hydoxyindoleacetic Acid |
| 9 | 5HT | 5-Serotonin |
| 10 | 5HTOL | 5-Hydroxytryptophol |
| 11 | 5HTP | 5-Hydroxytryptophan |
| 12 | A | Adenine |
| | AM | Acetaminophen |
| 13 | ASC | Ascorbic Acid |

TABLE 6-continued

DESCRIPTION OF SCORING VARIABLES

| Variable Number | Abbreviation | Name or Possible Characteristic |
|---|---|---|
| 14 | CYS | Cysteine |
| 15 | DA | Dopamine |
| 16 | DOPAC | Dihydroxyphenylacetic Acid |
| 17 | EPI | Epinephrine |
| 18 | G | Guanine |
| 19 | GR | Guanosine |
| 20 | GSH | Glutathione (reduced) |
| 21 | HGA | Homogentisic Acid |
| 22 | HVA | Homovanillic Acid |
| 23 | HX | Hypoxanthine |
| 24 | KYA | Kynurenic Acid |
| 25 | KYN | Kynurenine |
| 26 | LD | L-Dopa |
| 27 | MET | Methionine |
| 28 | MHPG | Methoxy-Hydroxyphenyl Glycol |
| 29 | NE | Norepinephrine |
| 30 | NMN | Normetanephrine |
| 31 | TPOL | Tyrptophol |
| 32 | TRP | Tryptophan |
| 33 | TYR | Tyrosine |
| 34 | TYRA | Tyramine |
| 35 | URIC | Uric Acid |
| 36 | VMA | Vanillylmandelic Acid |
| 37 | XAN | Xanthine |
| 38 | P01 | Methoxyhydroxybenzene |
| 39 | P02 | Cysteine or Methionine Di Peptide |
| 40 | P03 | Catechol- |
| 41 | P04 | Catechol- |
| 42 | P05 | Cysteine Condensation or Peptide |
| 43 | P07 | Cysteine Condensation or Peptide |
| 44 | P08 | TRP or TYR Peptide |
| 45 | P09 | TRP or TYR Peptide |
| 46 | P10 | Indole- |
| 47 | P11 | Indole- |
| 48 | P12 | Methoxybenzene |
| 49 | P13 | Indole- |
| 50 | P14 | Hydroxybenzene |
| 51 | P15 | TYR or TRP Peptide |
| 52 | P16 | TYR or TRP Peptide |
| 53 | P17 | Indole- |
| 54 | P18 | Hydroxyindole- |
| 55 | P19 | Hydroxyindole- |
| 56 | HVA_A | Oxidative of Backwave of HVA |
| 57 | TPR_A | Oxidative of Backwave of TRP |
| 58 | TYR_A | Oxidative of Backwave of TYR |
| 59 | XAN_A | Oxidative of Backwave of XAN |
| 60 | 1 | TRP/5HIAA + 5HTOL + 5HT + 5HTP |
| 61 | 2 | TRP/OHAN + KYN |
| 62 | 3 | TRP/KYN + HTP + HTOL + 5HIAA + 5HT |
| 63 | 4 | HTP/5HIAA |
| 64 | 5 | 5HIAA/5HTOL |
| 65 | 6 | KYN/OHKY |
| 66 | 7 | HVA/5HIAA |
| 67 | 8 | TYR/HPLA |
| 68 | 9 | TYR/HVA + LD + E + NE + MHPG + DA + 3MT + NMN |
| 69 | 10 | HVA/MHPG |
| 70 | 11 | TYR/HPLA + HVA |
| 71 | 12 | XAN/HVA |

Testing the Algorithm on AD vs. Controls

Figure 3:
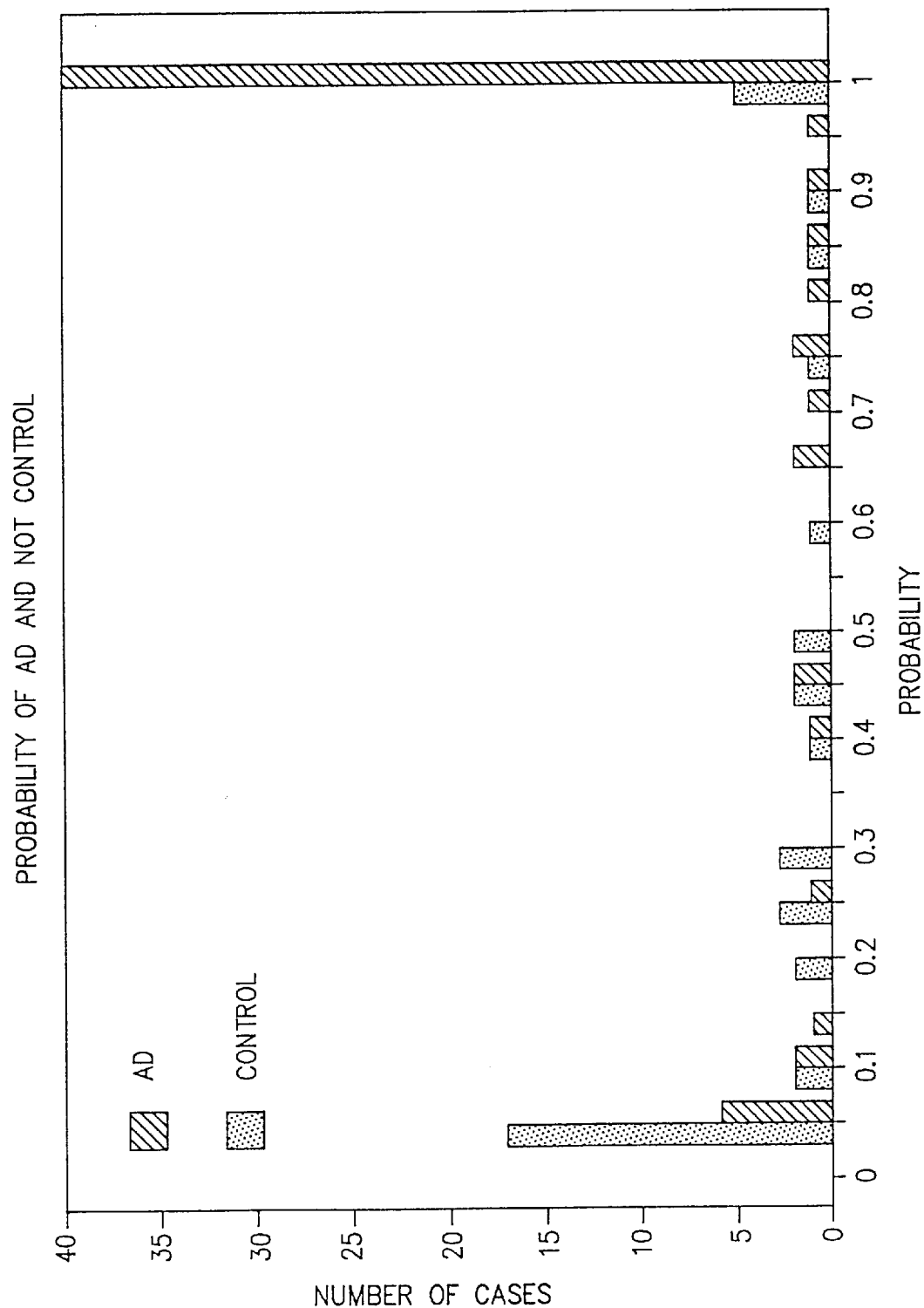
FIG. 3 is a plot showing initial scoring of Alzheimer's Disease v. control.

For an initial test, conditions were set up such that each individual sample was evaluated as if the data base were set up without its contribution. The results of the initial scoring are shown in FIG. 3. The scoring of five of the 61 AD cases as controls (p=less than 0.01 that the sample is an AD and not a control) is not surprising given the probable diagnostic error rate in AD. The scoring of 4 of the controls as AD are of concern.

Figure 4:
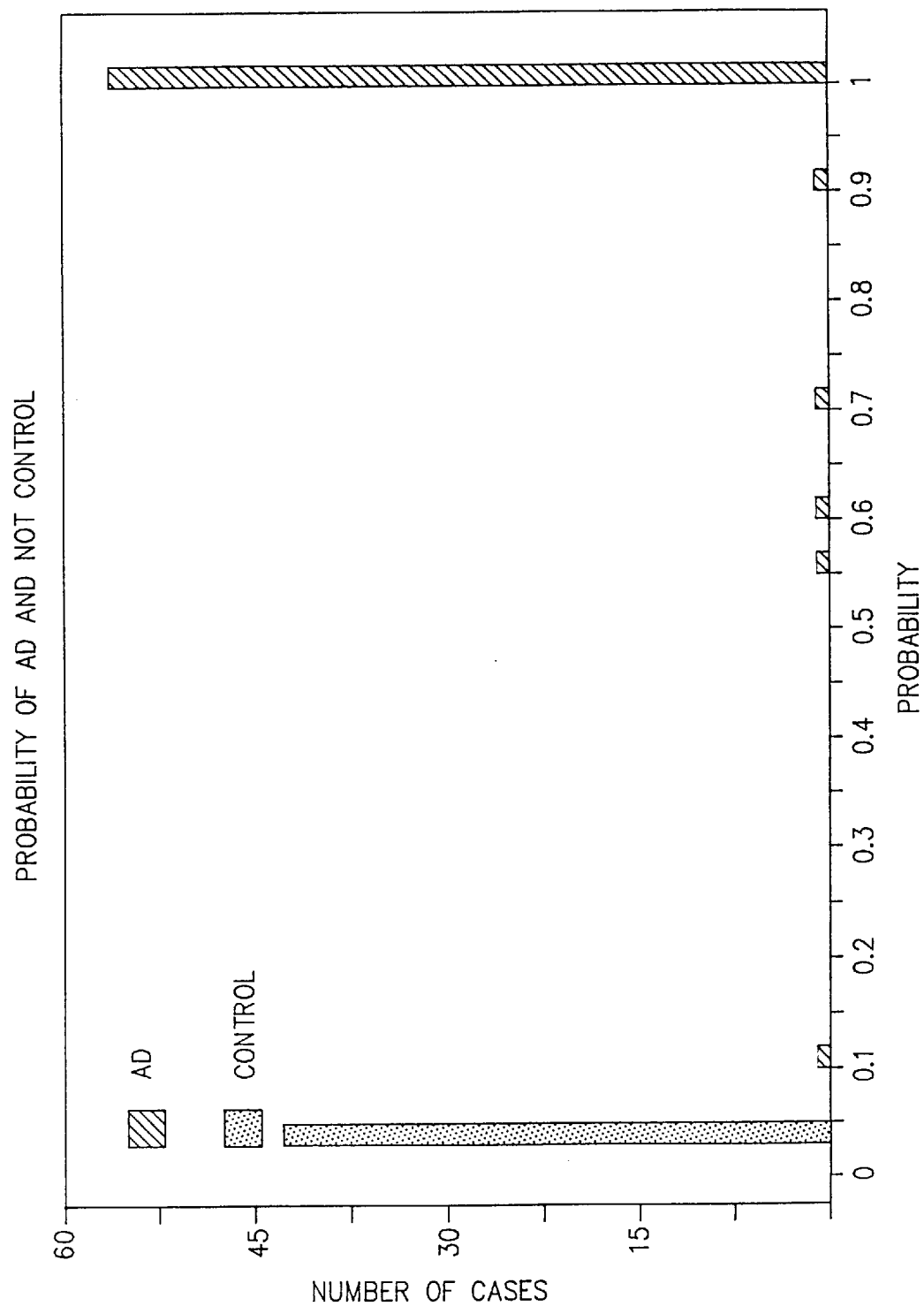
FIG. 4 is a plot similar to FIG. 3, with five Alzheimer's Disease cases which scored as controls removed from the Alzheimer's Disease scoring Distribution.

One possible explanation is that the AD data base is in effect contaminated by five cases that clearly do not match the overall AD profile and are probably not AD. When these five samples are removed from the AD data base and all samples, including the 5 removed, are scored, the control and AD groups are uniquely separated as shown in FIG. 4. The five samples that were removed from the AD scoring data group distribute in an equivocal region from 0.1 to 0.9. In subsequent application of the procedure and algorithm to AD samples vs. all other samples (PD, SC, HD, PSP and C) in the data base asking the question is this sample in the AD distribution and not in the distribution of all others yielded similar results scoring AD samples with p values=0.98 or greater. The distribution of scores of all others was scattered from 0.001 to 0.8 including the 5 AD samples which previously scored in this region vs. controls.

Testing PD vs. Controls and PD vs. AD

Figure 5:
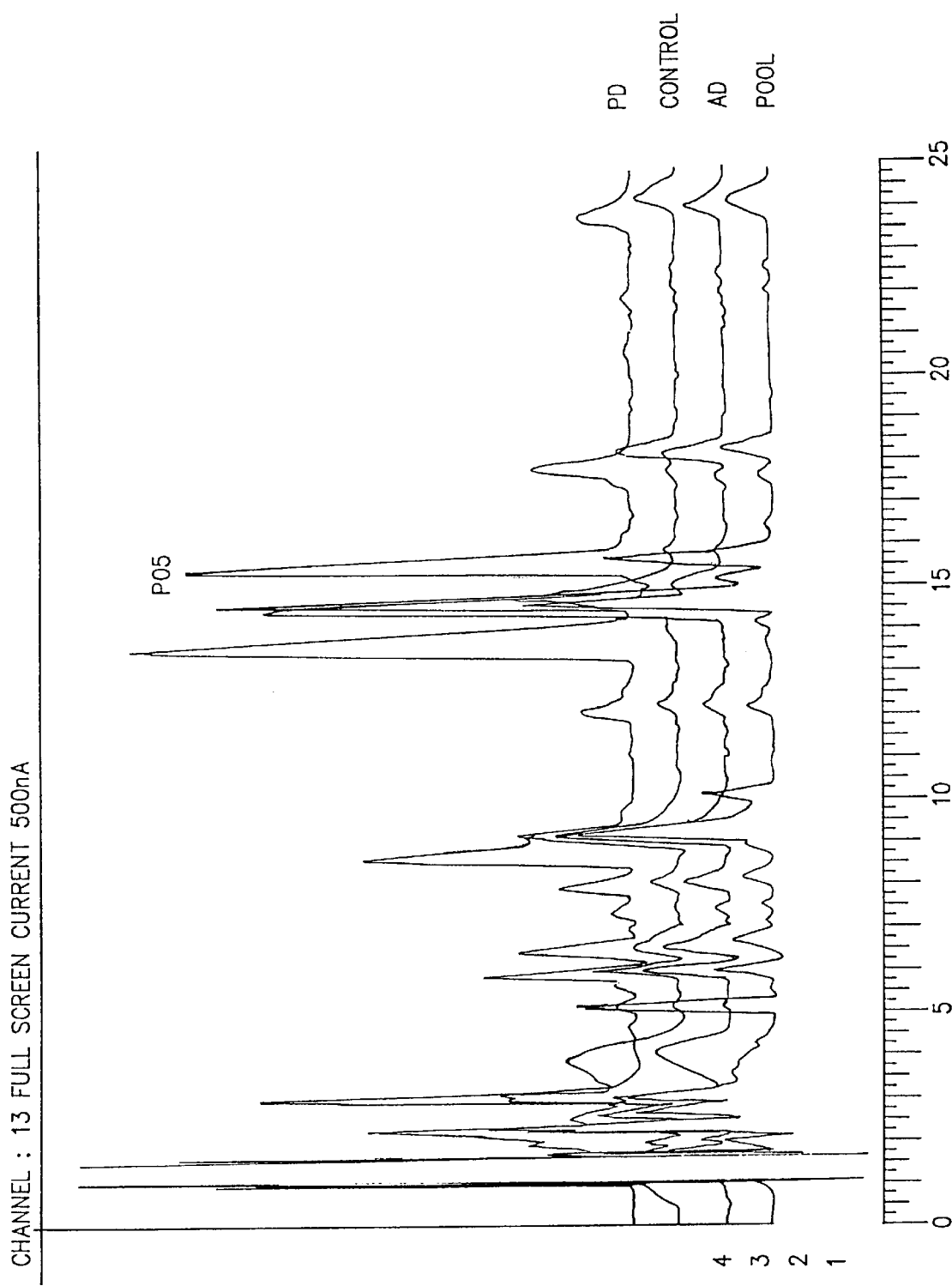
FIG. 5 is a plot showing analog distribution measurements in accordance with the present invention.

Eighteen unknown peaks were initially selected for assay in all samples because of differences among preliminary pools of AD Alzheimer's Disease, Parkinson's Disease, C control samples and SC schizophrenia. Of these, six occurred only in one sample of the group and 11 had distributions of only slight differentiation capability. One peak, designated PO5 shown in FIG. 5, occurred predominantly in the PD group. Otherwise, values above 100% of pool values were seen in only six of the AD group. The mean values of PO5 and S.D. relative to a pool value of 100 were PD 415±200, Control 20±15, AD30±80, and SC 28±17. This one variable utilized alone in the distribution p scoring algorithm separates PD from controls with PD values from 0.4–0.999 and C values from 0.51–0.001. With all variables, the PD values were all greater than 0.994 and C values less than 0.003.

Scoring AD and not PD without PO5 separated 58 PD samples with scores of less than 0.02 and two with scores of 0.14 and 0.18. 55 AD samples scored above 0.98 with six in the region between 0.25 and 0.76, including the 5 cases which initially scored as controls. Including PO5 in the scoring, all PD samples scored below 0.001. 57 of the AD samples scored above 0.98 and 4 of the initial 5 that matched the control group scored near the PD samples from 0.11 to 0.32.

EXAMPLE II

Pathological Changes in the Olfactory System in Alzheimer's Disease

In Alzheimer's Disease a number of studies have shown that the structures of the limbic system, including entorhinal cortex, hippocampal formation, basal forebrain and the amygdala are the most severely affected areas of the brain. Since the amygdala, entorhinal cortex and uncal hippocampus are strongly related to olfactory input (Pearson et al Anatomical correlates of the distribution of the pathological changes in the neocortex in Alzheimer's disease. Proc. Natl. Acad. Sci. 82: 4531–4524, 1985) suggested that the olfactory pathways may not be the initial site of pathology in the disease. In fact some authors have suggested that inhaled molecules, such as aluminosilicates, could contribute to the etiology of the disease (Roberts, E. Alzheimer's disease may begin in the nose and may be caused by aluminosilicates. Neurobiol, Aging. 7:561–567, 1986; Shipley M. T. Transport of molecules from nose to brain; transneuronal anterograde and retrograde labelling in the rat olfactory system by wheat germ agglutinin-horseradish peroxidase applied to the nasal epithelium. Brain Res. Bull. 15: 129–142, 1985; Peri D. P., Good P. F. Uptake of aluminum into central nervous system along nasal-olfactory pathways. Lancet 1: 1028, 1987).

The olfactory nerve cells in the olfactory epithelium project through the cribiform plate to the olfactory bulb (Kosel et al, Olfactory bulb projections to the parahippocampal area of the rat. J. Comp. Neurol. 198: 467–482, 1981) Primary olfactory fibers synapse in olfactory glomeruli with descending dendrites of mitral and tufted cells; which are the primary output neurons of the bulb. Axons of mitral and tufted cells enter the olfactory tract and provide input to the anterior olfactory nucleus, as well as to the central projections of the olfactory system. The anterior olfactory nucleus, located in the center of the bulb, gives rise to a recurrent collateral to the bulb and to a crossed projection to the anterior commissure. The olfactory tract passes through the anterior perforated substance and projects to prepiriform cortex, corticomedial nuclei of the amygdala, entorhinal and perirhinal cortices, inferior surface of the frontal lobe, insula, temporal pole and basal forebrain (Haberty et al, The anonal projection patterns of the mitral and tufted cells in the olfactory bulb in the rat. Brain Res. 129: 152–157, 1977).

Several lines of evidence have shown that the olfactory system is affected in ALzheimer's Disease. Several groups have shown that Alzheimer's Disease patients show deficits in olfactory recognition (Doty et al, Presence of both odor identification and detection deficits in Alzheimer's Disease. Brain Res. Bull. 18: 597–600, 1987; Green, J. E., Songsan- and P., Corkin S., Growdon J. H. Olfactory capacities in Alzheimer's Disease. Neurology 39, Suppl 1: 138, 1989; Rezek D. L. Olfactory deficits as a neurologic sign on dementia of the Alzheimer type. Arch. Neurol. 44: 1030–1032, 1987). A study which examined patients with very mild Alzheimer's Disease showed impairment on a task of identification of odors, however olfactory thresholds were normal (Koss et al, Olfactory detection and identification performance are dissociated in early Alzheimer's Disease. Neurology 38: 1228–1232, 1988). Pathologic studies have recently documented changes in the primary olfactory receptor neurons in Alzheimer's Disease. Talamo et al, Pathological changes in olfactory neurons inn patients with Alzheimer's Disease. Aging 7: 11–14, 1976 reported nasal epithelium from Alzheimer's Disease patients showed increased immunoreactivity for phosphorylated neurofilaments, as well as Tau and Alz-50 positive neurites. These neurons however did not contain neurofibrillary tangles. Neurite formation in the olfactory epithelium did correlate with numbers of neurofibrillary tangles and senile plaques in the hippocampus of the Alzheimer's Disease brains. The possibility of using biopsy of nasal epithelium as a clinical marker of Alzheimer's Disease during life was suggested.

Pathological studies of the olfactory bulb in Alzheimer's Disease have shown consistent changes. Esiri and Wilcock, (The olfactory bulbs in Alzheimer's Disease. J. Neurol. Neurosurg. Psychiatr. 47: 56–60, 1984.) (1984) found neurofibrillary tangles in the olfactory bulb in the tufted cells, outer granule cells, and in the anterior olfactory nucleus. Hyman and collegues (Pathological changes in the olfactory system in aging and Alzheimer's disease. Int. Study Group for the Pharmacology of Memory Disorders) (1991) has examined 10 control and 10 Alzheimer's Disease olfactory bulbs. Large numbers of neurofibrillary tangles were consistently found in the Alzheimer's Disease anterior olfactory nucleus, with only small numbers in the mitral and tufted cells. This is consistent with other primary sensory systems in Alzheimer's Disease in which higher order association areas show more severe pathology than primary sensory areas.

The olfactory epithelial neurons and olfactory bulb have been shown to contain very high levels of carnosin (β-alanyl-L-histidine), and several studies have shown that carnosine is released in the olfactory bulb in response to peripheral inputs (Macrides et al, The olfactory bulb. In: Emson P. C. (ed.) Chemical Neuroanatomy, Raven Press, New York, pp. 391–426, 1983). The external tufted cells in the olfactory bulb contain dopamine, substance P or both. The deeper tufted cells may use excitatory amino acids. Periglomerular cells contain GABA, enkephalin or dopamine. The olfactory bulb receives a very strong centrifugal projection including enkephalin, vasoactive intestinal polypeptide, LHRH, somatostatin and substance P fibers. A cholinergic projection originates mainly in the ventral nucleus of the diagonal band. Serotonergic projections originate from the dorsal raphe nuclei, while there is a noradrenergic projection from the locus ceruleus. The olfactory bulbs therefore receive a rich and variegated neurochemical input, including projections from the cholinergic, noradrenergic and serotonergic nuclei which are known to be affected in Alzheimer's Disease (Macrides et al, The olfactory bulb. In: Emson P. C. (ed) Chemical Neuroanatomy, Raven Press, New York, pp. 391–426, 1983).

Several factors relating to the suitability of using nasal secretions for neurochemical analysis have been examined. These include sample acquisition, potential effects of bacterial or viral infection, the specific compounds which can be identified, and means for normalizing the data to compensate for sampling variability and sample size.

Figure 6A:
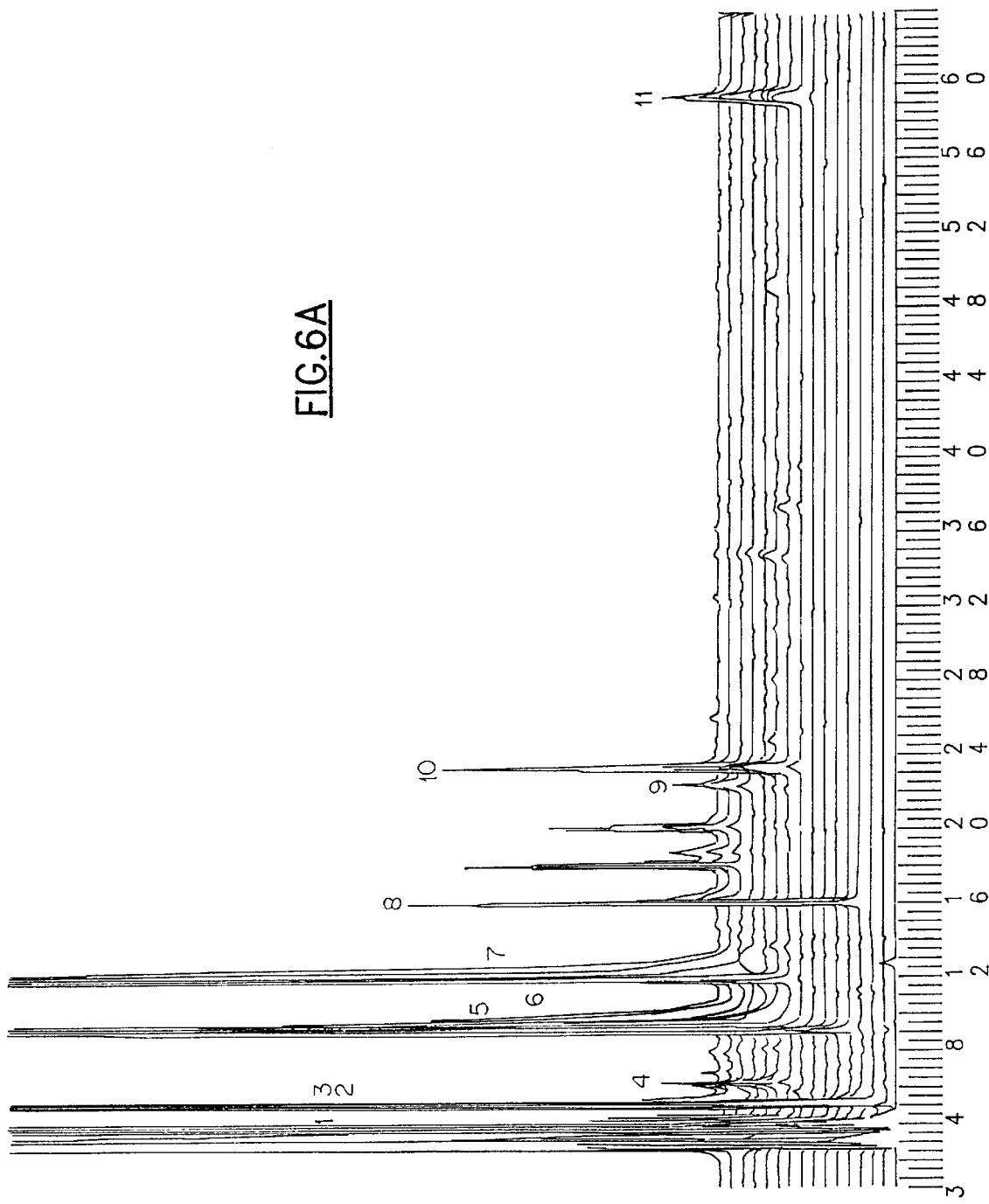
FIG. 6A is a plot of measurements of nasal mucosa swab samples at low gain.
Figure 6B:
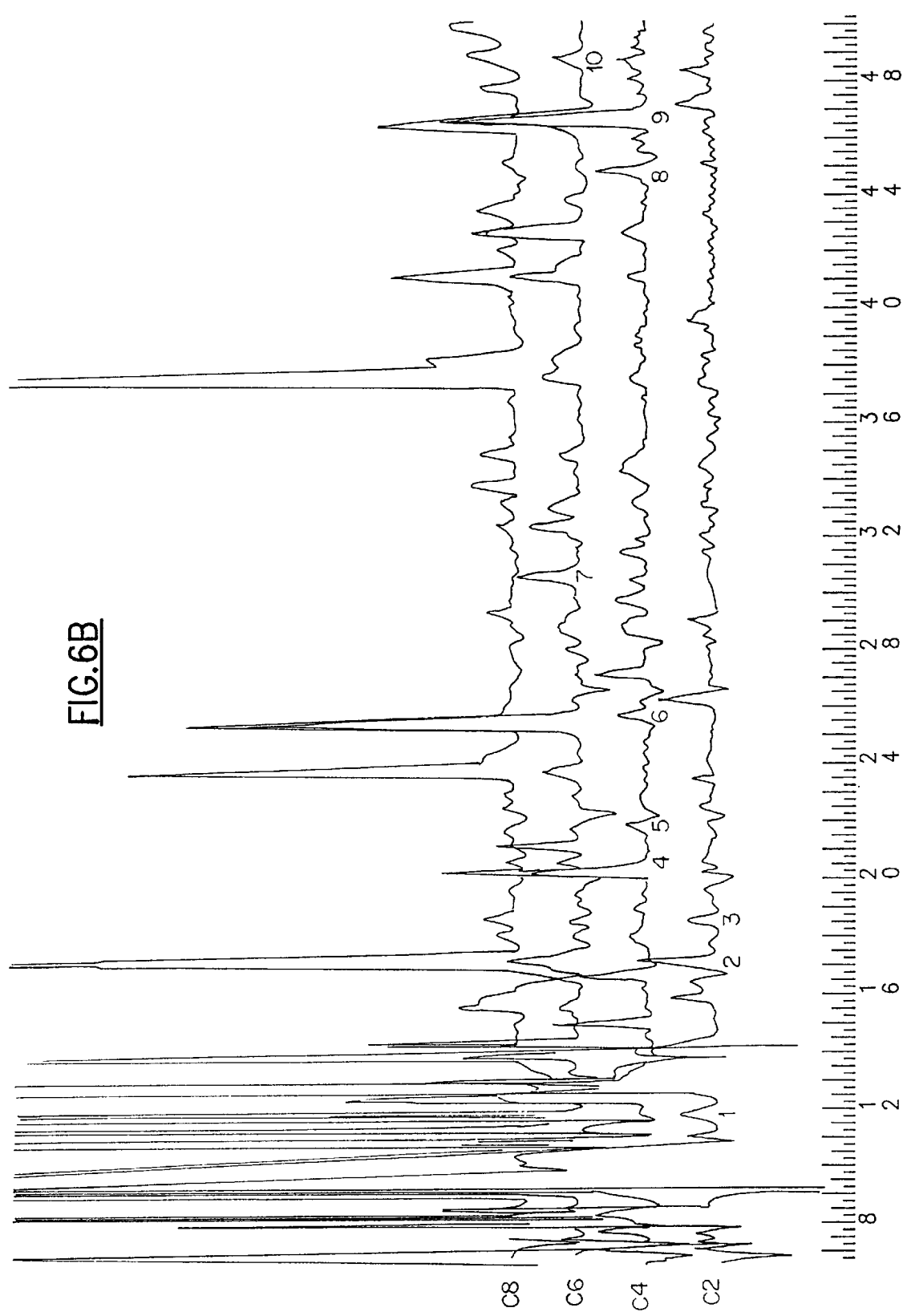
FIG. 6B is a plot of nasal mucosa swab samples at high gain.

Following the electrochemical analysis procedure above described for CSF all the compounds listed in Table 2 have been identified using nasal secretion samples although the concentration profiles are significantly different than for CSF. (See typical patterns in FIGS. 6A and 6B.) Notably, dihydroxyphenylacetic acid (DOPAC) is present in greater concentrations than homovanillic acid (HVA) and serotonin (5HT) is relatively equivalent to 5-hydroxindoleacetic acid (5HIAA). Also notably different is the complexity of the region of small di- and tri-peptides with retention times of 30–45 min on channels 10–15. Essentially, the nasal mucosa appear to contain representative compounds from all metabolic pathways that occur in the neuronal projections to the olfactory bulb.

Figure 7:
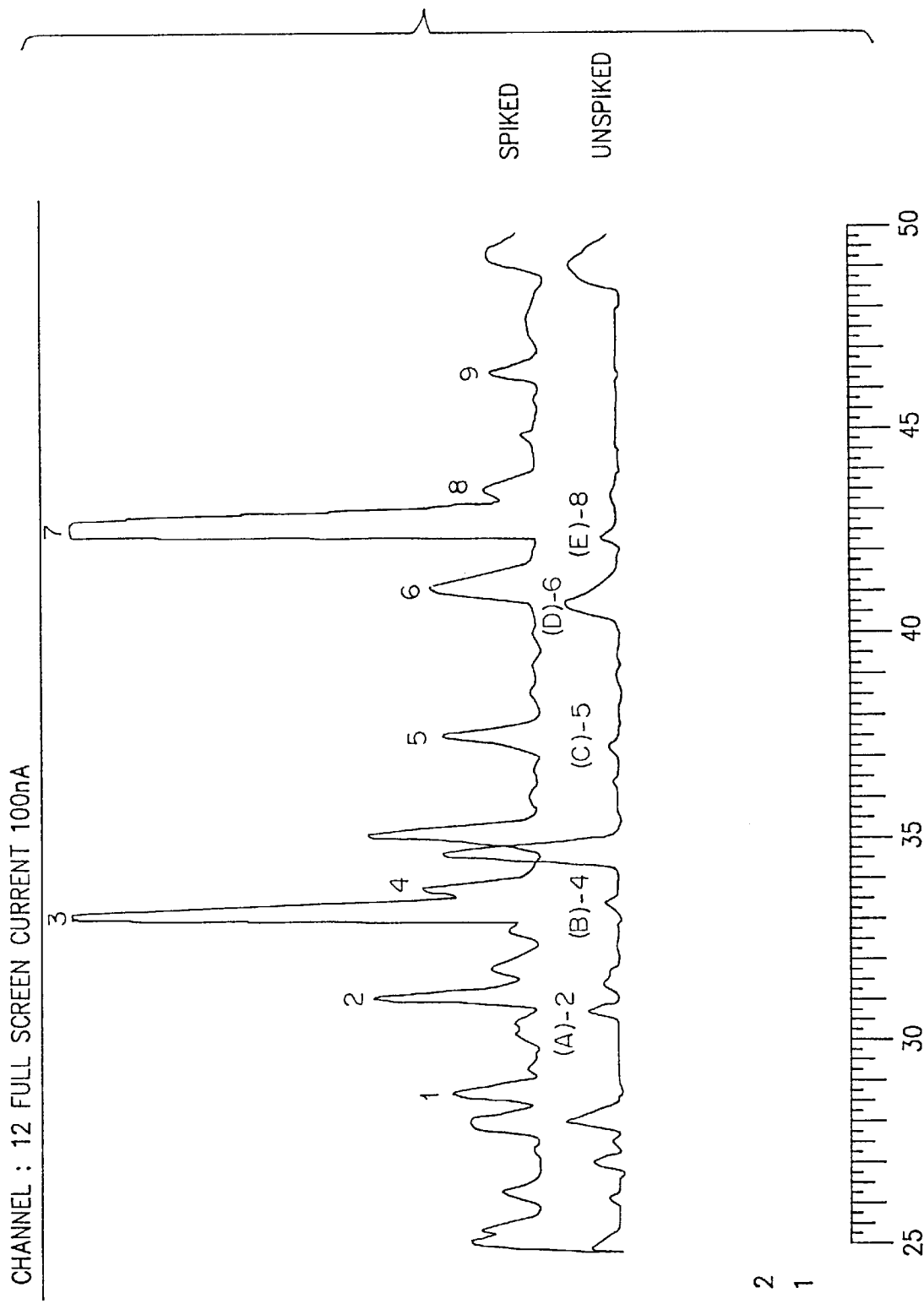
FIG. 7 is a plot of β-amyloid in saline suspension of mucosa swab.

Two characteristics make nasal secretions attractive for neurochemical analysis. The secretions are close to the site or origin of the compounds being measured and they are in a strong reducing environment. Oxidation potential measurements of saline suspensions of nasal secretions with platinum vs. Ag/Ag/cl yield values from −0.230 to −0.300 mV compared to lumbar CSF values of −0.050 to −0.170. The reducing character of the tissue is consistent with observation of a large number of easily oxidized peaks on the lower channels of the chromatographic pattern. The reducing character of the sample makes it highly attractive for clinical use because of the stability inferred for the target compounds. Indeed preliminary studies indicate no change in 5-hydroxyindoleacetic acid or homovanillic acid over 24 hours in perchloric acid extracts at room temperature. From the number of peaks in the 35–50 min region, the nasal mucosa also appear to be a stable matrix for small peptides, including fragments of β-amyloid peptide. This hypothesis was tested by incubating β-amyloid in saline suspensions of nasal mucosa and observing the development over 6 hours of electroactive peaks, five of which corresponded to original peaks in the suspension as shown in FIG. 7.

Sample Acquisition Preparation and Normalization

Samples typically weigh approximately 100 mg. A preliminary evaluation of swabs taken from high in the nostril, approximately 2 cm, vs. a wipe of the nares at approximately 0.5 cm, indicate that all species of interest are present lower in the nose, but at significantly reduced concentrations overall. In an initial study from an n of 4 there were no significant changes in the ratio of DOPAC/HVA or in tryptophan (TRP) to kynurenine (KYN), but the ratio of 5HIAA/5HT increased, consistent with reduced concentrations of 5HT in swabs obtained lower in the nose. Similarly, on an n of 4, a relatively aggressive scrubbing the swab yields a pattern with higher concentrations than a more gentle scrub, but without significant changes in overall pattern.

Swabs were extracted by cutting the tip and placing it in 300 $\mu$l of 0.1 M $HClO_4$, they ere vortexed for 1 min. centrifuged and then reextracted in another 300 $\mu$l of 0.1 M $HClO_4$. Further sequential extractions did not result in any improvement in recoveries. Following centrifugation the pellets are combined, and can be extracted with 40:60 acetonitrilehexane for analysis of ubiquinones and larger peptides.

Several brands of cotton swabs were evaluated for blank effects. Of these, plastic handled Johnson and Johnson (™) swabs proved clean enough to be used as received. Paper composite and wooden handles of various types showed a number of small peaks that have the potential to inferfere with the target compounds of interest.

The selection of appropriate divisors or normalizers of the data is a major consideration since sample size is not controllable. This issue was investigated in a preliminary study of 6 individuals from whose left and right nostril swabs were obtained. From the initial data analysis, xanthine (XAN), uric acid (UA), tyrosine (TYR), DOPAC, HVA, TRP, KYN, 5HIAA and 5HT have been measured. The 6 left and right individual samples as duplicate pairs coefficient of variation were from ±60–±80%. When all data was divided by xanthine, the variations were ±15–±30%. When precursor product ratios were used, the variations were further lowered (DOPAC/HVA mean 1.4±7%; TRP/KYN mean 2.6±14%; and 5HT/5HIAA mean 1.1±13%)

Possible Effects of Bacterial and Viral Infections

Two available cultures of Pseudomonas and Staphlococcus were evaluated to look for possible interferences from bacterial infection. Aliquots of approximately 10 mg wet weight of cultured bacteria isolated by centrifugation and washing were sonified in 200 $\mu$L of 0.1 M $HClO_4$, centrifuged and the supernatant analyzed. Responses for XAN, KYN, TYR, TRP, guanosine and hypoxanthine were observed of approximately 50–100% of the response of a typical nasal swab. No dopaminergic, serotonergic, or noradrenergic metabolites were observed. Consequently, it is thought that bacterial contamination would have to be quite massive, constituting over 10% of a typical sample ot have a 10% or greater effect on the measurements.

In the initial study three of the six subjects had colds and there were no significant differences between them and unaffected individuals. There was a slight, but not statistically significant increase in KYN/XAN and a decrease in TRP/KYN ratios.

It thus appears that nasal secretions may advantageously be employed as samples for neurochemical analysis using electrochemical detection techniques. Similar results were found using platelets.

Moreover, the invention advantageously may be employed for diagnosing a disease condition at an early stage, i.e. before observable physical manifestations. For example, in the case of Alzheimer's Disease, the exact etiology is unknown. However, there is strong evidence that genetic factors play a role (St. George-Hyslop et al, Genetic linkage studies suggest that Alzheimer's disease in not a single homogenous disorder. Nature 347: 194–197, 1990). The means by which a genetic defect contributes to the pathologic features of the illness is unclear. A major feature of the pathology is the accumulation of the β-amyloid protein in senile plaques, blood vessels, skin and other peripheral tissues (Joachim et al, Clinically diagnosed Alzheimer's disease: autopsy results in 150 cases. Ann. Neurol. 24: 50–56, 1988). By correlating changes in neurochemical markers with changes in accumulation of the β-amyloide protein as the Alzheimer's Disease progresses, it is possible to provide an early diagnosis for Alzheimer's Disease. Also, identification of neurochemical markers for Alzheimer's Disease may provide a basis for prevention and/or treatment, i.e. by identifying precursors, progression of the disease may be slowed, stopped or even reversed.

The invention has been described for use in diagnosing Alzheimer's Disease. It will be understood, however, that the invention advantageously may be used to diagnose and characterize other neurological, degenerative or defective disorders such as Huntington's Disease, Parkinson's Disease, schizophrenia, progressive supernuclear palsy, amyotrophic lateral sclerosis and senile dementias. The invention also advantageously may be used to classify and diagnose tumors, carcinomas, cardiovascular abnormalities and other disorders, or for selection of therapy based on categories of known successful vs. unsuccessful outcomes. Moreover, both treatment protocols and new pharmaceuticals may be evaluated.

Still other changes and advantages will be obvious to one skilled in the art.

What is claimed is:

1. In a method for screening disorders in a test patient in which biological samples containing electrochemically active molecular constituents from normal, unafflicted control individuals, afflicted, abnormal individuals, and said test patient are electrochemically analyzed to generate electrical signal patterns representative of said electrochemically active molecular constituents of said samples, the improvement which comprises creating a data base of electrical signal patterns representative of the frequency distribution of a plurality of predetermined electrochemically active constituents of biological samples from an epidemiologically significant number of individuals having known categories of disorders and from said unafflicted control individuals, and comparing said electrical signal patterns in said data base for conformity to electrical signal patterns representative of the frequency distribution of said predetermined constituents of a fluid sample from said test individual to screen said disorders in said test patient.

2. A method according to claim 1, wherein said samples comprise body fluid.

3. A method according to claim 2, wherein said body fluid comprises cerebrospinal fluid.

4. A method according to claim 2, wherein said body fluid comprises plasma.

5. A method according to claim 2, wherein said body fluid comprises blood containing platelets.

6. A method according to claim 2, wherein said body fluid comprises nasal mucosa.

7. A method according to claim 2, wherein said body fluid comprises serum.

8. A method according to claim 2, wherein said body fluid comprises saliva.

9. A method according to claim 2, wherein said body fluid comprises urine.

10. A method according to claim 1, wherein each electrical signal pattern representative of frequency distribution of said plurality of predetermined constituents of said biological samples is generated by the following steps, comprising: passing each one of said biological samples separately through a liquid chromatographic column for achieving time-space separation of said constituents of said biological sample eluting in the column and an electrochemical detection apparatus for generating electrical signals representative of the electrochemical pattern of said biological sample.

11. A method according to claim 10, wherein said plurality of predetermined constituents of said biological samples are separated by electrochemical characteristics in said electrochemical detection apparatus.

12. A method according to claim 1, wherein one of said known categories of disorders comprises Alzheimer's Disease.

13. A method according to claim 1, wherein one of said known categories of disorders comprises Parkinson's Disease.

14. A method according to claim 1, wherein one of said known categories of disorders comprises Huntington's Disease.

15. A method according to claim 1, wherein one of said known categories of disorders comprises schizophrenia.

16. A method according to claim 1, wherein one of said known categories of disorders comprises Progressive Supernuclear Palsy.

17. A method according to claim 1, wherein one of said known categories of disorders comprises amyotrophic lateral sclerosis.

18. A method according to claim 1, wherein one of said known categories of disorders comprises senile dementis.

19. A method according to claim 1, wherein one of said known categories of disorders comprises tumors.

20. A method according to claim 1, wherein one of said known categories of disorders comprises carcinomas.

21. A method according to claim 1, wherein one of said known categories of disorders comprises cardiovascular abnormalities.

22. A method for screening disorders in a living subject organism, and including electrochemically analyzing biological samples including electrochemically active compounds taken from healthy organisms and from organisms suffering from a known disorder, said analysis comprising passing each one of said biological samples separately through a liquid chromatographic column for achieving time-space separation of said electrochemically active compounds of said sample eluting from said column and an electrochemical detection apparatus to generate electrical signal patterns representative of the frequency distributions of said electrochemically active compounds, examining said patterns for chaotic or non-linear values, electrochemically analyzing a biological sample taken from said subject organism to generate electrical signal patterns representative of the frequency distribution of electrochemically active compounds of said sample from said subject organism, comparing the patterns of said subject's sample for conformity with said chaotic or non-linear values.

23. A method according to claim 22, wherein characteristics of said electrochemically active compounds represented by said electrical signal patterns comprise biochemical characteristics.

24. A method according to claim 23, wherein said characteristics of said electrochemically active compounds represented by said electrical signal patterns comprise electrochemical measurements of neurotransmitters and analogous compounds.

25. A method according to claim 23, wherein said electrical signal patterns comprise electrochemical measurements of neurotransmittors and analogous compounds.

26. A method according to claim 23, wherein said electrical signal patterns comprise electrochemical measurements of cofactors and analogous compounds.

27. A method according to claim 23, wherein said electrical signal patterns comprise electrochemical measurements of precursors and analogous compounds.

28. A method according to claim 23, wherein said electrical signal patterns comprise electrochemical measurements of metabolites and analogous compounds.

29. A method according to claim 22, wherein said disorder is Alzheimer's Disease, and said electrochemically active compounds comprise tryosine and tryptophan peptide degradation fragments from beta amyloid.

30. A method according to claim 22, wherein said disorder is Parkinson's Disease, and the characteristics of said electrochemically active compounds represented by said electrical signal patterns comprise electrochemical measurements to determine the presence of PO5.

31. A method for screening disorders in a living subject organism, and comprising electrochemically analyzing biological samples including electrochemically active compounds taken from healthy organisms and from organisms suffering from a known type of disorder, said analysis including passing each one of said biological samples separately through a liquid chromatographic column for achieving time-space separation of said electrochemically active compounds of said samples eluting from said column and an electrochemical detection apparatus to generate an electrical signal pattern representative of said electrochemically active compounds, creating a data base of electrical signal patterns representative of frequency distribution of said electrochemically active compounds from said biological samples, subjecting a biological sample from said subject organism to chromatographic separation and electrochemical analysis to produce electrical signal patterns representative of the frequency distribution of electrochemically active compounds in said subject organism's sample, and comparing the resulting electrical signal patterns of the analysis of said subject organism to said patterns in said data base for conformity therewith.

32. A method for screening Alzheimer's Disease in a living subject organism and comprising electrochemically analyzing, biological samples including electrochemically active compounds taken from healthy organisms and from organisms suffering from Alzheimer's Disease, said analysis including passing each one of said biological samples separately through a liquid chromatographic column for achieving time-space separation of said electrochemically active compounds of said samples eluting from said column and an electrochemical detection apparatus to generate electrical signal patterns representative of said electrochemically active compounds, creating a data base of electrical signal patterns representative of frequency distribution of said electrochemically active compounds from said biological samples, subjecting a biological sample from said subject organism to chromatographic separation and electrochemical analysis to produce electrical signal patterns representative of the frequency distribution of electrochemically active compounds in said subject organism's sample, and comparing the resulting electrical signal patterns from the analysis of said subject organism to said patterns in said data base for conformity therewith.

* * * * *